United States Patent [19]

Andersen et al.

[11] 3,981,701

[45] Sept. 21, 1976

[54] METHOD AND APPARATUS FOR CONTROLLING A VOLATILE SUBSTANCE

[75] Inventors: Harold Willids Andersen; Charles H. Harrison, both of Oyster Bay, N.Y.

[73] Assignee: H.W. Andersen Products Inc., Oyster Bay, N.Y.

[22] Filed: Aug. 10, 1973

[21] Appl. No.: 387,461

[52] U.S. Cl. .................................. 62/49; 62/129; 73/40.7
[51] Int. Cl.² ......................................... F17C 13/02
[58] Field of Search ............... 62/45, 125, 129, 48, 62/49; 220/9 LG; 43/40.7; 61/.5

[56] References Cited
UNITED STATES PATENTS

| | | | |
|---|---|---|---|
| 3,163,013 | 12/1964 | Webster | 62/49 X |
| 3,280,620 | 10/1966 | Anderson | 62/125 X |
| 3,364,729 | 1/1968 | Yearwood | 73/40.7 |
| 3,727,418 | 4/1973 | Glazier | 62/45 |
| 3,798,919 | 3/1974 | Hershner, Sr. | 62/45 |
| 3,812,888 | 5/1974 | Dalton | 62/49 X |

*Primary Examiner*—William F. O'Dea
*Assistant Examiner*—Ronald C. Capossela
*Attorney, Agent, or Firm*—Frank J. Jordan

[57] ABSTRACT

In controlling a volatile substance, for example in controlling the release of ethylene oxide for use in a sterilization apparatus, the volatile substance is contained under pressure in a confined system and the latter is immersed in a fluid. The fluid is capable of absorbing the volatile substance such that if any of the volatile substance leaks from the confined systems into the immersion fluid, physicochemical changes will occur in the immersion fluid. These physicochemical changes may be sensed by various detecting devices which thereby serve to detect leaks of volatile substance from the confined system. The immersion fluid may be used as a heat transfer medium in heat exchange relationship with the confined system and desired associated control elements such as a pressure regulator to thereby prevent undesirable condensation of the volatile substance.

11 Claims, 1 Drawing Figure

U.S. Patent  Sept. 21, 1976  3,981,701
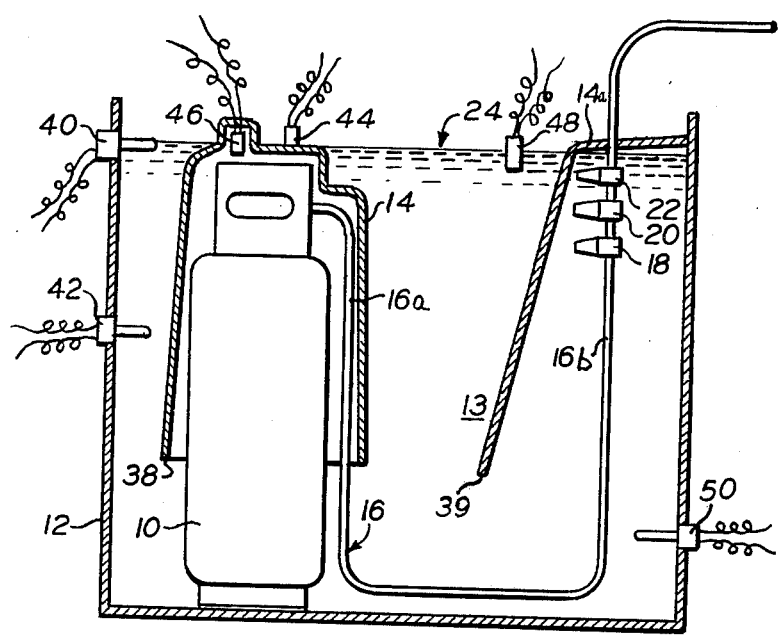

METHOD AND APPARATUS FOR CONTROLLING A VOLATILE SUBSTANCE

BACKGROUND OF THE INVENTION

A reliable method of sterilization includes utilizing saturated steam in a suitable pressure autoclave. High temperature dry heat has also been proven as a reliable method of sterilization. However, both of these methods of achieving sterilization are severly degrading to a wide variety of materials used in the medical and allied fields. For example, most plastics, virtually all paper based items, optical instruments, electronic items, adhesive products, and many essential medical/hospital products are all irreparably damaged by exposure to sterilizing conditions in saturated steam or dry heat. Although it is rarely used in hospitals, industrial use of various forms of radiation sterilization is common in many European countries, but the radiation doses commonly used have severe detrimental effects on many materials, particularly plastics such as vinyl (polyvinyl chloride) and Teflon (polytetra fluoroethylene).

In contrast to sterilization by utilizing heat and radiation, the use of conventional gaseous sterilization, particularly ethylene oxide (1, 2 epoxy-ethane) gas, has greatly reduced the adverse effects on even the most sensitive materials when it is used in the standard vacuum/pressure sterilization cycle in a pressure vessel. Even though these cycles are normally processed at temperatures slightly elevated above room temperature, the mild heat usually does not degrade most materials which are sensitive to heat. It is common for these moderate temperature vacuum/pressure cycles to inject additional water vapor to control the relative humidity within the pressure vessel and maintain it at a value as near saturation as possible. This is necessary in order to prevent or compensate for possible dehydration of bacterial spores which makes then extra-resistant to sterilization by ethylene oxide gas.

All of the above and other problems and compensations are largely avoided by sterilizing with ethylene oxide at room temperature. Room temperature ethylene oxide sterilization was heretofore made possible in economically practical and physically compatible form for use in hospitals by the introduction of a system of sterilization known as ANPROLENE (Registered Trademark of H. W. Andersen Products, Inc.,) as fully described in U.S. Pat. Nos. 3,476,506; 3,552,083 and in other pending patent applications. This known system of sterilization employs the methods of controlling a gaseous sterilant through the use of membranes of controlled permeability through which the ethylene oxide gas diffuses at a controlled and predictable rate. Wide experience in the hospital and associated medical fields has proven the suitability of room temperature ethylene oxide sterilization.

The use of gaseous sterilants in industrial processes is also widely known. Most of these utilize the familiar vacuum/pressure cycle in a pressure chamber designed for the purpose. The slightly elevated temperature generally used, and the rehumidification water vapor injected into the chamber, do not severly damage a wide variety of medical products. However, vacuum/pressure vessels suitable for industrial use are necessarily massive in construction in order to withstand the forces involved and are both costly to install and costly to operate. The physical characteristics of these known vacuum/pressure cycles requires packaging material which is capable of not only gently releasing the air entrapped within the package during the initial vacuum portion of the sterilization cycle, but of greater importance, must permit adequate penetration of the sterilant to every remote fold and crevice of the contents of the package. In order to absolutely assure that every microbe within the contents of the gas sterilization chamber has been reached and sterilized by the gas, cycle times must of necessity be long, typically 8 to as long as 24 hours. It is understandably costly to tie up these massive chambers for such long sterilization cycles. Where the product of unit being sterilized is small, the unit cost per cycle is acceptably low and economical, however, as unit size increases, the number of units which can be processed per sterilization cycle is reduced and the apportioned unit cost of sterilization and bacteriological sterilization controls increases rapidly.

An economical alternative to chamber sterilization is a process knows as the STERIJET process (Registered Trademark of Sterilcoa, Inc.) which is described in U.S. Pat. Nos. 3,516,223; 3,630,665; 3,564,861 and 3,597,934. The STERIJET process produces vacuum packaged sterile items commonly used in the medical and allied fields, including some aspects of the food industry, for example, spices. Packaging material for the STERIJET process is usually flexible, conformal, and designed to enhance the skin tight appearance of a hermetically, vacuum sealed package. Even the slightest packaging defect or damage to the microbiological contamination barrier will be evidenced by the loss of the skin tight appearance of the vacuum packaged conformal membrane. This loss of vacuum tight appearance is a signal to the user or interim inspector that the sterility of the contents at that time must be suspect.

One of the design problems that had to be solved for this known STERIJET system is the sterilant gas control method used to assure that each unit that is vacuum packaged sterile receives exactly the correct predetermined quantity of gas sterilant. Among the possibilities, such as volumetric measurement and constant volume-variable pressure, the method of controlling delivered volume by use of constant pressure, constant system impedance to flow (an orifice) and variable time of sterilant gas flow has been found to be the most reproducible method of regularly delivering the same quantity of gas. This system requires that the system delivery pressure remain constant during the use of the machine. Several methods of achieving this are fully described in the aforementioned United States Patents.

Ethylene oxide is capable of existing both as a liquid and a gas when confined under pressure. If the atmosphere within a pressure vessel is entirely ethylene oxide, it can exist both as a liquid and a gas, with an interface between the two. The pressure within the vessel will be entirely determined by the temperature of the liquid and the gas, assuming essentially isothermal conditions, and providing the contents of the several are entirely pure ethylene oxide. This physical phenomena is a well known characteristic of liquid/gaseous vapor interfaces, and need not be further explained in detail. Thus, it may be seen, if it is desired to control the pressure of such a system as a constant, it is necessary to control the temperature of the liquid gas interface and keep it constant.

However, if gaseous sterilant is withdrawn or delivered by the system, for example to packages to be sterilized, the instantaneous pressure during the withdrawal will decrease, causing some of the liquid to evaporate to gas to maintain the pressure of the gas. This evaporation causes a cooling of the liquid/gas interface, which reduces the temperature at the interface and hence the gas pressure above the interface. Under normal conditions, the quantity of heat stored in the balance of the liquid, restores the liquid gas interface to nearly its former temperature by thermal convection currents within the liquid. Repeated withdrawal of gaseous sterilant will cause a gradual but continued reduction of the temperature, and therefore the pressure within the vessel unless a quantity of heat is transferred to the liquid by some integral or external means that is sufficient to replace the heat of evaporation.

This heat of evaporation could be replaced by several means. For example, heaters could be placed directly in contact with the ethylene oxide; heat transfer fluids could be circulated either by thermal convection or by forced, pumped circulation, through heat exchange pipes in the sterilant tanks; the sterilant could be directed through an external heat exchanger as an evaporator or boiler and recondensing the vapor or gas in the tank, thus releasing the heat of condensation within the tank; the sterilant tank itself could be immersed in a heat transfer fluid, either as a closed or open system, depending on the heat transfer fluid chosen; heat could be transferred by radiant energy, either from a light or electromagnetic source; the sterilant tank could be heated by the condensation of a heat transfer fluid on the exterior of the sterilant tank or by condensing the heat transfer vapor within heat exchanger means within the tank; heat could be transferred by conduction, convection and radiation from electrical heaters placed on the outside of the sterilant holding vessel; and with varying degrees of success, by almost any heating method.

Most sterilants, such as ethylene oxide, propylene oxide and similar agents, are very reactive molecules. Of principle concern in the management, storage, and control of sterilants, are oxidation, self reaction such as polymerization, and possible reaction with the materials of construction used in the manufacture of storage, piping, and other sterilant system components.

Many sterilants, ethylene oxide included, are readily oxidizable, and thus flammable. Ethylene oxide, for example, is flammable in concentrations of 3% in air to 80% in air under normal conditions. It is of prime concern, therefore, that any sterilant system designed for the management of ethylene oxide be well designed to prevent ignition of ethylene oxide under both normal operating conditions, and in the event of any foreseeable equipment failure or malfunction. Prevention of ignition can be accomplished in several ways: removal of all sources of ignition, which is the usual precaution; encapsulation of sources of ignition in sealed housings which are impervious to flame fronts, including internal pressurization to prevent entry of flammables; enforced dilution which absolutely prevents attaining flammable concentrations; absolute containments of any possible leakage, either by use of mechanically secure systems which are usually all welded, or by containment of the complete system within an overenclosure which will contain and vent any leaks to a non-hazardous discharge point.

The present invention relates to a method and apparatus for controlling sterilant gas pressure. An additional feature of the present invention is that all components of the system that are under pressure, and hence might be a source of accidental leakage of the sterilant into the surrounding atmosphere, are contained within an absorbent medium capable of containing even large leakage rates, and signalling the fact of leakage by automatic audible or other alarm, giving more than adequate time for corrective action to be taken by supervisory or maintenance personnel.

According to the present invention a method of safely managing flammable gases, particularly sterilants such as ethylene oxide, involves completely immersing the pressurized portion of the system under an absorbtive fluid. In the case of ethylene oxide, an example of a suitable fluid is water, treated to enhance the absorption of ethylene oxide. Under standard conditions, water will absorb up to 4.5% of ethylene oxide by volume and the mixture will remain nonflammable. A specific feature of the method according to the present invention is the placing of an inverted open ended vessel over the components containing ethylene oxide under pressure such that the vessel is itself immersed in the fluid. The depth of immersion is not of substantial importance, however, the benefits to be obtained in this unique method are realized if initially, the immersion fluid is drawn completely into the inverted vessel by removing all air or other gases that may have been entrapped during the inverting. This may be accomplished by simple temporary venting or by withdrawing the gas by pressure differentials such as vacuuming.

It has been demonstrated that a leak of a sterilant such as ethylene oxide, which occurs under such an inverted immersed vessel will be quickly absorbed into the immersion fluid. If the leak occurs at a substantial rate, the gas continues to be absorbed into the surrounding fluid until the local dissolved concentration exceeds the limit of solubility, at which point the gas collects under the inverted open end vessel, forcing the locally saturated immersion fluid down in the inverted vessel. At the extreme, the entrapped gas will again pass under the lip of the inverted vessel where it will be absorbed in the surrounding fluid, which has not been locally saturated.

At each stage of this development there are physicochemical changes occuring which can be sensed to signal the existance of a leak. for example, the dissolving ethylene oxide will cause a change in the specific gravity of the immersion fluid which can be detected automatically. The pH of the fluid will also change. At the point where the local limit of solubility has been reached, the leaking sterilant will form a collection of gas. This may be detected by a change in bouyancy of the inverted vessel; a change in liquid level outside the immersed vessel; a change in the thermoconductivity of the fluid from a liquid to a gas. There are undoubtedly other changes of lesser importance.

According to the present invention, the immersion fluid is also the heat transfer medium. It may be maintained at a temperature which will ensure adequate sterilant pressure. Because the temperature of the sterilant supply will be reduced by the heat of evaporation as the sterilant is converted from its liquid storage state to its gaseous delivery state, the pressure of the sterilant will tend to decrease as its temperature decreases. This must be offset by heat transfer from the immersion fluid. This heat transfer can be accelerated by maintaining fluid circulation within the immersion medium. Thermal convection currents will exist, and it may be advantageous to augment these with forced flow by a pumping means.

In order to assure the most constant delivery pressure possible, the apparatus of this method also employs a self-compensating pressure regulator. It has been shown that it is necessary to maintain this pressure regulator within the temperature of the immersion fluid and heat transfer medium. If the pressure regulator and its associated dispensing valves are permitted to cool to a temperature lower than the condensation temperature, liquid ethylene oxide will collect in the piping at these cooler points and will be carried with the sterilant gas stream, thereby substantially increasing the amount of sterilant delivered to the package to be sterilized and possibly causing damage to the product from liquid sterilant's solvent action.

Other features which are considered as characteristic for the invention are set forth in the appended claims.

Although the invention is illustrated and described in relationship to specific embodiments, it is nevertheless not intended to be limited to the details shown, since various modifications and structural changes may be made therein without departing from the spirit of the invention and within the scope and range of equivalents of the claims.

The construction and method of operation of the invention, however, together with additional objects and advantages thereof will be best understood from the following description of specific embodiments when read in connection with the accompanying drawing.

SUMMARY OF THE INVENTION

In controlling a volatile substance, for example in controlling the release of ethylene oxide for use in a sterilization apparatus, the volatile substance is contained under pressure in a confined system and the latter is immersed in a fluid. The fluid is capable of absorbing the volatile substance such that if any of the volatile substance leaks from the confined systems into the immersion fluid, physicochemical changes will occur in the immersion fluid. These physicochemical changes may be sensed by various detecting devices which thereby serve to detect leaks of volatile substance from the confined system. The immersion fluid may be used as a heat transfer medium in heat exchange relationship with the confined system and desired associated control elements such as a pressure regulator to thereby prevent undesirable condensation of the volatile substance.

BRIEF DESCRIPTION OF THE DRAWINGS

The drawing is a schematic elevational view, partly in section, of an arrangement for managing and controlling a volatile substance according to one embodiment of the invention.

DESCRIPTION OF THE PREFERREDD EMBODIMENTS

The drawing shows a storage tank 10 filled with a sterilant under pressure which, by way of example, may include ethylene oxide. The storage tank 10 may be filled with a liquid under pressure with a liquid/gas interface and gas under pressure above the interface.

The storage tank 10 is placed in a vessel 12 filled with an absorbtive fluid 13 which is capable of absorbing sterilant of the type included in storage tank 10. Thus, when the storage tank 10 contains ethylene oxide, the absorbtive fluid may be water which will absorb up to 4.5% of ethylene oxide by volume and the mixture will remain nonflammable.

An inverted open ended vessel 14 may be placed over the storgage tank 10 so that the vessel 14 is itself immersed in the fluid 13.

The depth of immersion of the vessel 14 may vary, however one preferred arrangement is to provide that initially the immersion fluid 13 is drawn completely into the inverted vessel 14 by removing all air or other gases from the latter that may have been entrapped during the inverting. This may be accomplished by temporary venting or by withdrawing the gas by pressure differentials such as vacuuming.

The storage tank 10 is provided with a delivery tube 16 which delivers the sterilant to apparatus or devices (not shown) which utilize the sterilant to effect sterilization of medical, surgical, dental and other products, instruments, tools, apparatus and the like. By way of example the sterilant may be delivered to sterilization apparatus of the type disclosed in U.S. Pat. No. 3,516,223 issued June 23, 1970.

As shown in the drawing the delivery tube 16 may be arranged in a U-shaped manner in which a portion of the down-leg 16a is disposed within the inverted vessel 14 and the up-leg 16b is provided with various control and safety devices. By way of example the latter devices may include a sterilant safety solenoid valve 18, sterilant pressure regulator 20, and a sterilant dispensing solenoid valve 22. An inverted open ended enclosure 14a may be attached to the side wall of vessel 12 and disposed over the immersed control and safety devices 18, 20, 22. The enclosure 14a has an opening through which the up-leg 16b passes with a suitable seal. The delivery tube 16 passes out of the absorptive liquid 13 through the sealed opening in the enclosure 14a and the non-immersed portion of the delivery tube may be utilized in connection with other safety, regulating and control devices.

It will be observed that the U-shaped portion of the delivery tube 16 and the control and safety devices 18, 20, 22 are disposed below the level 24 of the absorptive fluid 13 so that any leak that may develop in the aforementioned immersed elements 16, 18, 20, 22 will be quickly absorbed into the immersion fluid 13.

A leak of a sterilant such as ethylene oxide, which occurs under the inverted immersed vessel 14 or enclosure 14a will be quickly absorbed into the immersion fluid 13. If the leak occurs at a substantial rate, the gas continues to be absorbed into the surrounding fluid 13 until the local dissolved concentration exceeds the limit of solubility, at which point the gas collects under the inverted open end vessel 14 or enclosure 14a, forcing the locally saturated immersion fluid down in the inverted vessel 14 or enclosure 14a. At the extreme, the entrapped gas will again pass under the lip 38 or 39 of the inverted vessel 14 or enclosure 14a respectively where it will be absorbed in the surrounding fluid 13 which has not been locally saturated.

At each stage of this development there are physicochemical changes occuring which can be sensed to signal the existance of a leak. Accordingly suitable sensing devices are provided to sense one or more of these physicochemical changes. Thus a sensing device indicated at 40 may be provided to sense the specific gravity of the immersion fluid. In this regard dissolving ethylene oxide in the immersion fluid (for example water) will cause a change in the specific gravity of the immersion fluid. Since the pH will also change, a sensing device 42 may be used to sense changes in pH values. At the point where the local limit of solubility of the sterilant gas in the immersion fluid has been reached, the leaking sterilant will form a collection of gas. This may be detected by a sensing device 44 sensing the change in buoyancy of the inverted vessel 14, a device (for example float switch 46) sensing a change in the liquid level within the immersed vessel 14 and a device (for example float switch 48) sensing a change in the liquid level in the vessel 12. The sensing device 42 may also be utilized to sense changes in the following physicochemical properties of the immersion fluid: conductivity, thermoconductivity, the amount of transmitted light, coefficient of refraction, coefficient of reflection, characteristics of the transmission of sonic energy, characteristics of the transmission of reflection of sonic energy, and other physicochemical changes.

The immersion fluid 13 may also be a heat transfer medium. Thus the immersion fluid 13 may be maintained at a temperature which will ensure adequate sterilant pressure. Because the temperature of the sterilant supply will be reduced by the heat of evaporation as the sterilant is converted from its liquid storage state to its gaseous delivery state, the pressure of the sterilant will tend to decrease as its temperature decreases. This must be offset by heat transfer from the immersion fluid. In this regard the immersion fluid 13 may be heated by a heater 50. This heat transfer canced accelerated by maintaining fluid circulation within the immersion medium. Thermal convection currents will exist, and it may be advantageous to augment these with forced flow by a non-illustrated pumping means.

In order to assure the most constant delivery pressure possible, the previously mentioned pressure regulator 20 is provided. It has been shown that it is necessary to maintain this pressure regulator 20, which is a self-compensating pressure regulator, within the temperature of the immersion fluid 13 which also serves as the heat transfer medium. If the pressure regulator 20 and its associated dispensing valves 18, 22 are permitted to cool to a temperature lower than the condensation temperature, liquid ethylene oxide will collect in the piping at these cooler points and will be carried with the sterilant gas stream, thereby substantially increasing the amount of sterilant delivered to the package to be sterilized and possible causing damage to the product from liquid sterilant's solvent action. Accordingly, the self compensating pressure regulator 20 along with its associated dispensing valves 18, 22 are disposed within the immersion fluid 13 which also serves as the heat transfer medium as previously described.

While the invention has been described by means of a specific example and in a specific embodiment it is not intended to be limited thereto for obvious modifications will occur to those skilled in the art without departing from the spirit and scope of the invention.

What we claim is:

1. The method of determining impairment of the containment and isolation integrity of a volatile substance contained and isolated under pressure within a closed storage tank comprising the steps of containing and isolating said volatile substance under pressure within a closed impervious storage tank, providing a man-made manufactured vessel, maintaining an immersion fluid within said vessel at a pressure lower than the pressure of the volatile substance in said closed storage tank, said immersion fluid being capable of absorbing said volatile substance, immersing said storage tank within said immersion fluid while maintaining the containment and isolation integrity between the volatile substance in said storage tank and the immersion fluid in said vessel, and sensing changes in said immersion fluid caused by absorption of said volatile substance by said immersion fluid upon accidental or other unintentional failure of containment and isolation integrity between said volatile substance in said storage tank and the immersion fluid in said vessel, and utilizing said sensed changes to determine impairment of the containment and isolation integrity of said volatile substance in said storage vessel.

2. The method according to claim 1 including controlling the release of said volatile substance from said storage tank.

3. The method according to claim 1 wherein said immersion fluid is water.

4. The method according to claim 1 wherein said immersion fluid is an aqueous solution.

5. The method according to claim 1 wherein said volatile substance includes ethylene oxide.

6. The method according to claim 1 including utilizing said fluid as a heat transfer medium in heat exchange relationship with said volatile substance.

7. The method according to claim 1 including the step of at least partially confining said storage tank and a portion of said immersion fluid in a container which is at least partially disposed in said immersion fluid, and utilizing said container to provide for sensing localized changes in said portion of said immersion fluid confined in said container.

8. The method according to claim 7 wherein said container has an open bottom, said step of confining said storage tank includes immersing said container in said immersion fluid with said open bottom disposed below the level of the immersion fluid.

9. The method according to claim 7 wherein said container is an inverted open ended vessel which surrounds said storage tank.

10. The method according to claim 7 including completely filling said container with said immersion fluid.

11. The method according to claim 7 wherein said container is filled with said immersion fluid, said immersion fluid in said container being capable of absorbing a finite quantity of said volatile substance.

* * * * *